United States Patent [19]

Womble et al.

[11] Patent Number: 4,763,523
[45] Date of Patent: Aug. 16, 1988

[54] ROLLER BEARING TESTING DEVICE

[76] Inventors: Coy G. Womble, 2502 Jefferson St., Paducah, Ky. 42001; John P. Watkins, Rte. 2, Box 339A, Vienna, Ill. 62995

[21] Appl. No.: 89,748

[22] Filed: Aug. 26, 1987

[51] Int. Cl.⁴ ............................................. G01N 29/04
[52] U.S. Cl. ....................................... 73/587; 73/593; 340/682
[58] Field of Search ......................... 73/587, 593, 660; 340/682, 683

[56] References Cited

U.S. PATENT DOCUMENTS

| | | | |
|---|---|---|---|
| 2,763,152 | 9/1956 | Birdsall | 73/593 |
| 3,033,018 | 5/1962 | Haggadone | 73/9 |
| 3,111,294 | 11/1963 | Werner | 246/246 |
| 3,116,044 | 12/1963 | Stanley | 246/246 |
| 3,139,743 | 7/1964 | Sturm | 73/593 |
| 3,182,513 | 5/1965 | Mulhaupt | 73/514 |
| 3,225,587 | 12/1965 | Gordon | 73/9 |
| 4,016,020 | 4/1977 | Ongaro | 156/75 |
| 4,050,292 | 9/1977 | Bloch | 73/593 |
| 4,446,734 | 5/1984 | Empson | 73/593 |

FOREIGN PATENT DOCUMENTS 0689440 6/1964 Canada ............................. 73/593

Primary Examiner—Stewart J. Levy
Assistant Examiner—Lawrence G. Fess
Attorney, Agent, or Firm—Michael Sand Co.

[57] ABSTRACT

A mobile device for testing an axle-mounted roller bearing of a railcar to determine possible defects in the bearing. A movable base plate has an electric motor, drive roller, a driven roller, and a plurality of leveling jacks mounted thereon. The motor actuates the driver roller and the leveling jacks raise the base plate to move the drive roller and driven roller into contacting engagement with the outer race of the roller bearing. The outer race of the bearing is rotated by the drive roller at a predetermined rate. Shock pulses of energy also known as an acoustic emission, are emitted by defects in the bearing. A probe which senses such emissions is connected by a cable to a monitoring instrument. The probe is placed on a test point having direct metallic contact with the bearing, whereby the monitoring instrument will measure the type and magnitude of shock pulses, if any, emanating from the bearing. These readings are used to determine the type and extent of possible defects present in the bearing.

20 Claims, 2 Drawing Sheets

ROLLER BEARING TESTING DEVICE

TECHNICAL FIELD

The invention relates to a roller bearing testing device and in particular to a device for testing an axle-mounted roller bearing of a railcar. More particularly, the invention relates to a testing device having a motor-driven roller which applies sufficient contact force to the bearing to rotate the outer race thereof, whereby acoustic emissions produced by the rotating bearing indicate possible bearing defects.

BACKGROUND ART

Rail hopper cars, which are typically used to transport goods such as coal, grain and other items by railroad, usually each have eight axle-mounted roller bearings. These bearings are subject to various types and degrees of failure, ranging from normal wear to extensive damage due to metal fatigue. Some companies own as many as several thousand of these railcars, thereby necessitating a reliable preventative maintenance program directed at railcar bearing failure. Early detection of potential bearing failure is essential to an effective preventative maintenance program, the purpose of which is to prevent catastrophic failure of bearings in service. Such a failure could result in a major train derailment with attendant possible injury to operating personnel and major damage to equipment.

The term "acoustic emission" is applied to the "shock pulse" which is emitted by material under stress. In a roller bearing, this pulse is generated when, for example, a crack develops in an inner or outer bearing race. Each time a roller crosses the crack it is stressed and a pulse is generated and transmitted into the adjacent mounting structure.

During the past years, work done in the aerospace industry has produced definite data showing a direct relationship between increased acoustic emissions and the onset of bearing failure. Additional research and development in the bearing industry has shown a relationship between certain types of emitted signals and specific types of bearing failure. Moreover, a direct relationship exists between the decibel level of the acoustic emission and the extent of damage existing within a bearing. By measuring, recording, and plotting these emissions, it is possible to determine the condition of a bearing and its rate of deterioration to predict and avoid catastrophic failures.

The current accepted method of testing roller bearings mounted on railcar axles involves removal of the axle-bearing-wheel assembly from the car. A mechanic then grasps the outer race of the bearing, slowly rotates it by hand, and depends upon his sense of feel to determine if any defects are present within that bearing. Should he "feel" a defect, the bearing is then dismantled, inspected, and repaired or replaced if necessary. Obviously, this method depends solely upon the skill of the individual mechanic and does not provide acceptable records for a reliable preventative maintenance program.

The proposed device of the invention for testing axle-mounted roller bearings utilizes the acoustic emission principles described above and involves the use of an apparatus to rotate the bearing being tested. Such a device has been developed to permit rotation of the bearing for subsequent testing by the acoustic emission principle. Use of the device does not require removal of the bearing from the axle or removal of the axle assembly from the railcar.

Numerous devices pertaining to wheel friction indicators, directed primarily to railcars for determining the condition of the bearings are shown in the known prior art. Some examples of such prior art are disclosed in U.S. Pat. Nos. 3,033,018; 3,111,294; 3,116,044; 3,182,513; and 4,016,020. However, equipment for rotating the bearing of a railcar to conduct acoustic emission tests is not disclosed.

There is no roller bearing testing device for axle-mounted roller bearings of a railcar of which we are aware which rotates the bearing of a railcar for the purpose of conducting acoustic emission tests without requiring movement of the railcar along the rail, removal of the bearing from the axle, or removal of the axle assembly from the railcar to carry out such tests.

DISCLOSURE OF THE INVENTION

Objectives of the invention include providing a roller bearing testing device for rotating axle-mounted roller bearings of railcars for monitoring the acoustic emissions from the roller bearings by rotating the bearing at a predetermined speed for conducting the acoustic emission tests.

Another objective of the invention is to provide a device which will enable accurate records to be obtained for a reliable preventative maintenance program to detect bearing failure, thereby eliminating the need for reliance on the skill of individual mechanics to discover such failures. A still further objective of the invention is to prevent catastrophic failure of bearings in service which could cause a train derailment possibly resulting in injury to operating personnel and damage to equipment.

A further objective of the invention is to provide a device for rotating a bearing whereby shock pulses emitted by the rotating bearing under stress are measured, recorded, and plotted, whereby the data may be compared to those readings obtained from bearings containing known defects to ascertain the specific type and extent of damage to the bearing, and the rate of deterioration thereof, and to predict and avoid bearing failures.

Still another objective of the invention is to provide a roller bearing testing device which does not require movement of the railcar along the rail, removal of the bearing from the axle, or removal of the axle assembly from the railcar for rotating the bearing to conduct the testing, and in which the testing may be completed by a single technician.

A still further objective of the invention is to provide a roller bearing testing device in which the device is mobile so that it may be easily moved to the bearing being tested by a single worker, and in which the device is constructed of inexpensive, simple components, including an electric motor, a pair of rubber rollers, and a plurality of leveling jacks, all mounted on a base plate.

These objectives and advantages of the invention are obtained by the mobile device for testing an axle-mounted roller bearing of a railcar, the general nature of which may be stated as including, first means for contacting and rotating the roller bearing; a motor for driving the first means to rotate the roller bearing; a base moveably supporting the first means and the motor; jack means mounted on the base for moving the first means into and out of contact with the bearing; and second means for monitoring shock pulses of energy emanating from the bearing when said bearing is rotated by the motor and first means to determine possible defects in said bearing.

BRIEF DESCRIPTION OF THE DRAWINGS

A preferred embodiment of the invention, illustrative of the best mode in which applicants have contemplated applying the principles, is set forth in the following description and is shown in the drawings and is particularly and distinctly pointed out and set forth in the appended claims.

Similar numerals refer to similar parts throughout the drawings.

BEST MODE FOR CARRYING OUT THE INVENTION

Figure 1:
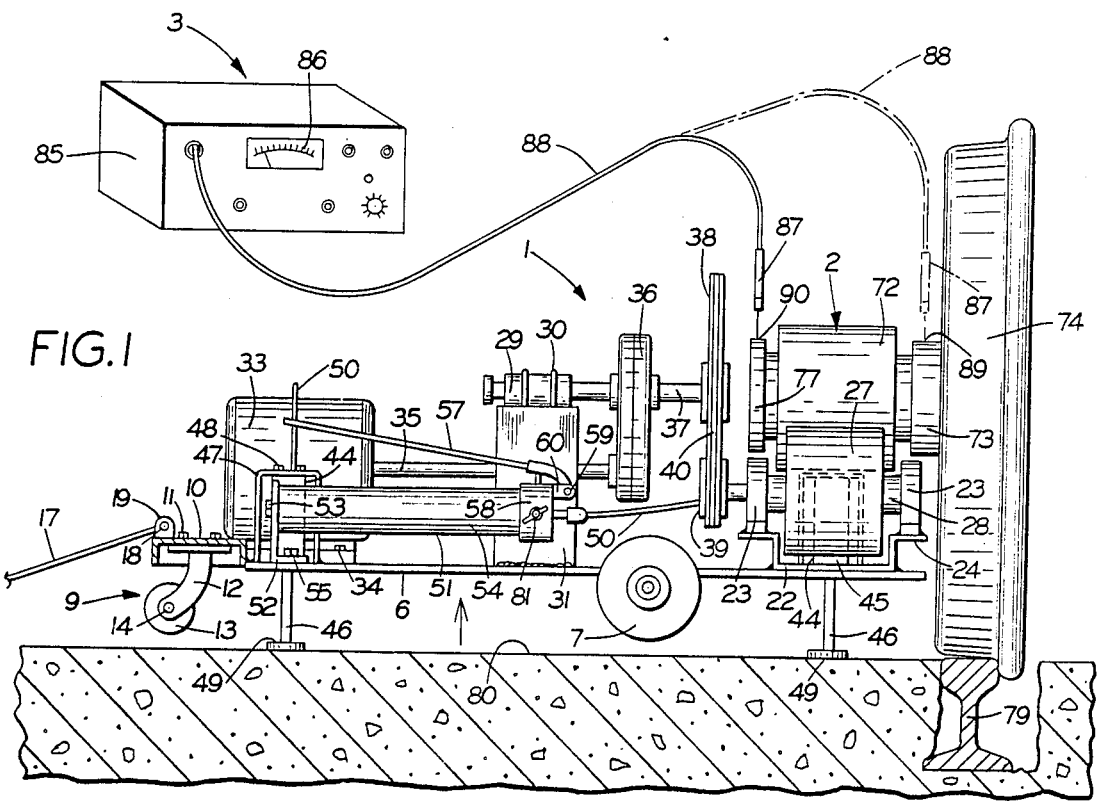
FIG. 1 is a side elevational view with portions in section of the roller bearing testing device of the invention, in a raised, engaged position with the axle-mounted roller bearing of a railcar, and with a probe of a monitoring instrument contacting a pair of test points on the bearing.

The roller bearing testing device of the invention is indicated generally at 1, and is shown particularly in FIGS. 1, 2, 4 and 5. The testing device is shown in its intended use, contacting and rotating an axle-mounted roller bearing 2 of a usual railcar (not shown) whereby shock pulses, also known as acoustic emissions, emanating from bearing 2 are measured by an acoustic emission bearing analyzer 3 to detect possible defects in the bearing.

Testing device 1 includes a generally L-shaped base plate 6 preferably formed of metal (FIGS. 1, 2, 4, 5 and 7) which is movably mounted by a pair of wheels 7 and a caster assembly 9. Wheels 7 are rotatably mounted on the ends of an axle 8 which is mounted on the bottom surface of base plate 6 and traverses the width thereof. Caster assembly 9 is mounted on an inside surface of the bottom of an inverted box-shaped extension 10 which extends outwardly from the rear of base plate 6 and which is secured thereto by welds 15. Caster assembly 9 has a swivel frame 12 which is mounted on extension 10 by a plurality of bolts 11. Swivel frame 12 has a caster 13 rotatably mounted thereon by a shaft 14. An elongated T-shaped handle 17 is pivotally mounted on extension 10 by a pivot pin 18 which passes through a pair of upwardly extending lugs 19 welded to extension 10 and through handle 17 which is inserted therebetween. Handle 17 is adapted to be manually grasped by a single worker for moving test device 1 to a position adjacent a bearing to be tested as described in greater detail below.

Figure 6:
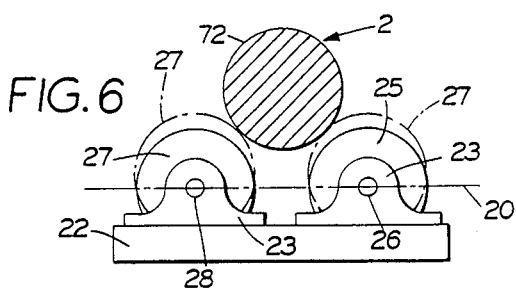
FIG. 6 is a diagrammatic view of the drive roller and idler roller of the testing device in full lines disengaged from the bearing and in dot-dash lines engaged with the bearing.

A generally U-shaped plate 22 is welded on the top surface of base plate 6 at the front thereof (FIGS. 1, 2, 4 and 5) for supporting four pillow blocks 23 and associated bearings 21. Blocks 23 preferably are welded to the top surface of horizontal flanges 24 of U-shaped plate 22. A freely rotatable idler roller 25 is mounted on a shaft 26 which is rotatably journaled in a pair of the pillow block bearings 21. A drive roller 27 is mounted on a shaft 28 which is rotatably journaled in the other pair of pillow block bearings 21. Rollers 25 and 27 preferably are formed of rubber and are mounted on the base plate in a horizontal spaced relationship, with the rotational axis of the rollers being parallel and in the same horizontal plane 20 as shown in FIGS. 2 and 6.

Drive roller 27 is driven by an electric motor 33 which is mounted on base plate 6 by a plurality of bolts 34 (FIGS. 1, 2, 4 and 5). An output shaft 35 of motor 33 extends frontwardly therefrom and is connected to a reduction gear 36. An output shaft 37 of reduction gear 36 extends frontwardly and rearwardly and is connected to a drive pulley 38. The rearwardly extending portion of shaft 37 passes through a bearing 29 which is mounted by a pair of U-bolts 30 on an upwardly extending support block 31 welded to base plate 6. Output shaft 35 of motor 33 passes through a bearing 32 also mounted on support block 31 by U-bolt 30. The mounting of bearings 29 and 32 of output shafts 37 and 35, respectively, on support block 31 provides stability to the motor and the reduction gear assembly of testing device 1. Drive pulley 38 is connected to a smaller diameter driven pulley 39 by an endless drive belt 40. A rearwardly extending portion of shaft 28 of drive roller 27 is connected to driven pulley 39 whereby drive roller 27 is rotated upon actuation of motor 33.

Base plate 6 of testing device 1 is raised and lowered into and out of engagement with a bearing to be tested, by three hydraulically actuated jacks 44. Each jack 44 includes a cylinder 45 and a piston 46 which extends downwardly and outwardly from cylinder 45 and through an opening 41 (FIG. 5) formed in base plate 6. Each jack 44 is mounted on an inverted generally U-shaped metal bracket 47, which is welded to the upper surface of the base plate. Jack cylinders 45 are attached to their respective brackets 47 by bolts 48. Each piston 46 has a horizontal foot or base 49 formed integrally on the outer end of the piston.

Two jacks 44 are mounted on the rear portion of base plate 6 in a spaced relationship, and the other of the jacks is mounted on the front portion of the base plate between idler roller 25 and drive roller 27. The jacks are connected by hydraulic fluid lines 50 to a manually operated hydraulic pump 51. Pump 51 is mounted on an L-shaped metal bracket 52 by a bolt 53 which passes through the bracket and a cylinder 54 of the pump. L-shaped bracket 52 is mounted on base plate 6 by a bolt 55 which passes through the bracket and the base plate. A pump handle 57 is pivotally mounted on cylinder head 58 by a pivot pin 59 which passes through a pair of lugs 60 which extend frontwardly from the cylinder head, and through the pump handle which is positioned therebetween. The operation of hydraulic jacks 44 and the components related thereto are described below.

Figure 2:
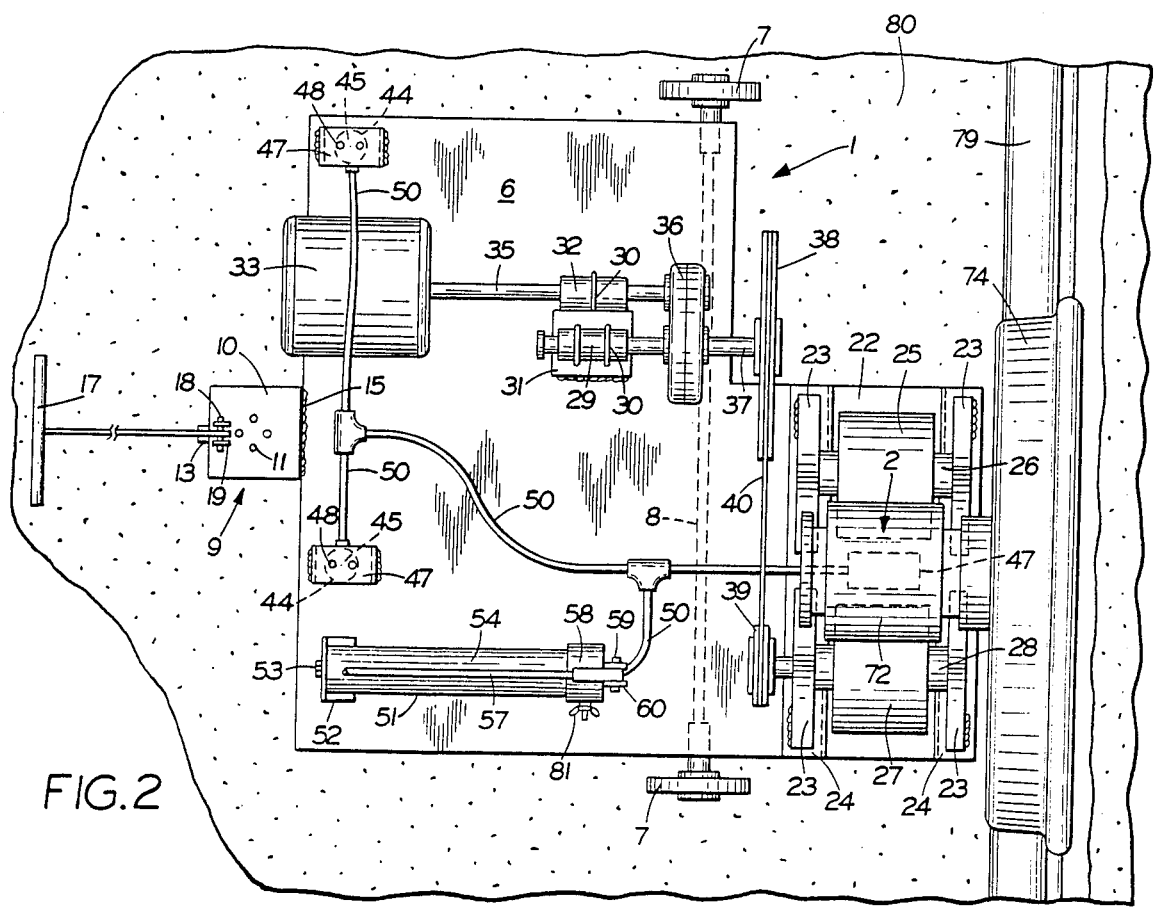
FIG. 2 is a top plan view of the testing device as shown in FIG. 1.
Figure 3:
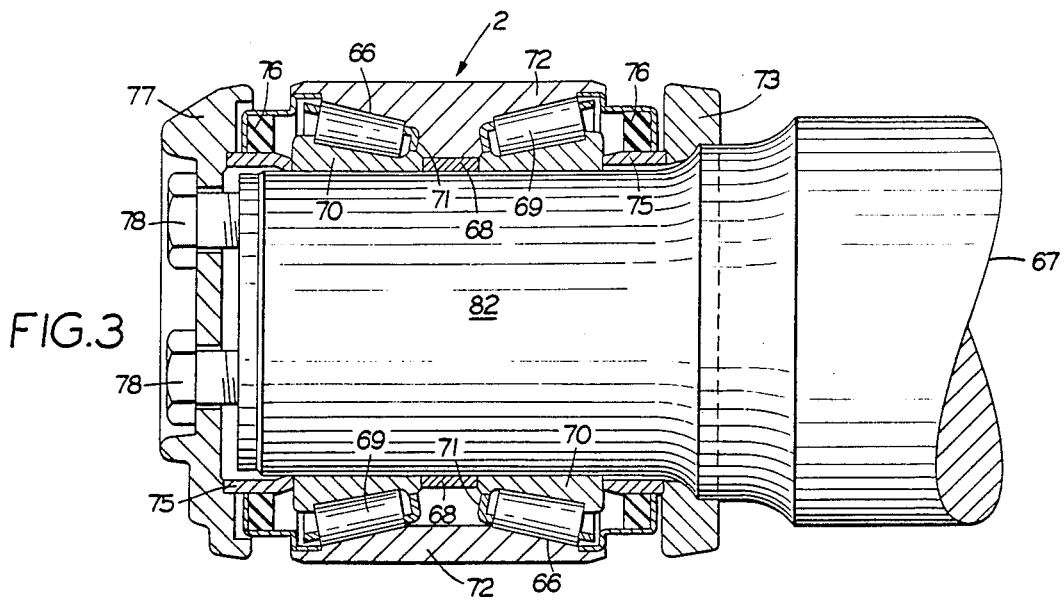
FIG. 3 is a greatly enlarged fragmentary view with portions in section, of an axle-mounted roller bearing of the type with which the testing device will be used.

Testing device 1 is adapted to rotate an axle-mounted roller bearing 2 of a railcar, particularly of the type shown in FIG. 3. Bearing 2 includes a pair of spaced roller assemblies 66 which are press-fitted onto the outer reduced diameter end 82 of an axle 67 of a railcar. The roller assemblies are maintained in a horizontal spaced relationship by a spacer 68 inserted therebetween. Each roller assembly 66 includes a plurality of rollers 69, an inner race 70 and a cage 71. An outer race 72 is rotatably mounted on the spaced roller assemblies in a usual manner. A backing ring 73 is mounted on inboard reduced diameter portion 82 of axle 67 to prevent movement of the bearing assembly toward a wheel 74 (FIGS. 1 and 2) of the railcar. A seal wear ring 75 and a seal 76 are positioned adjacent each roller assembly 66 to prevent dirt, water or other materials from contaminating the roller assemblies and to maintain lubrication in the bearing. The bearing assemblies are prevented from moving toward the outboard end of the axle by an end cap 77 and cap screws 78.

Figure 4:
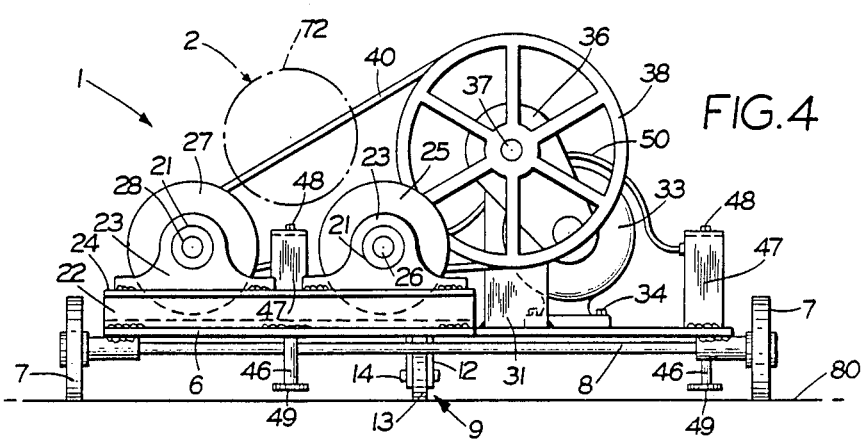
FIG. 4 is a front elevational view of the testing device, in a lowered, disengaged position from the bearing which is shown in dot-dash lines.
Figure 5:
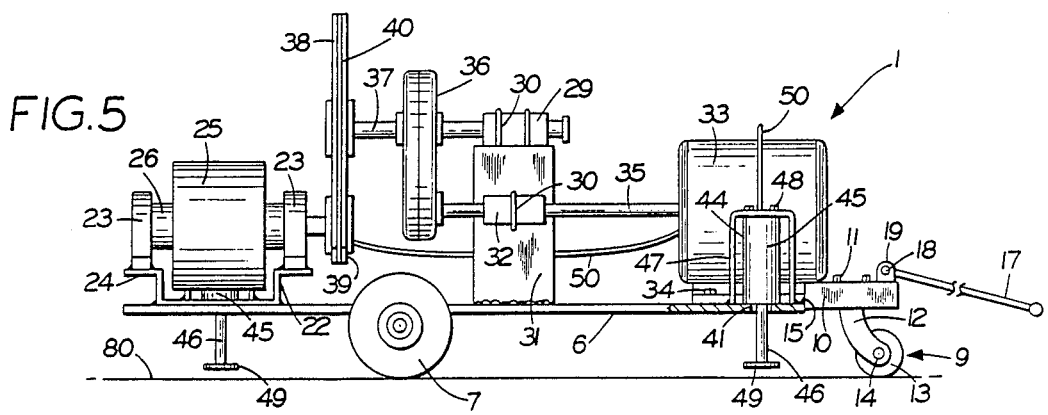
FIG. 5 is a reduced side elevational view opposite to that of FIG. 1 of the testing device in a lowered disengaged position.
Figure 7:
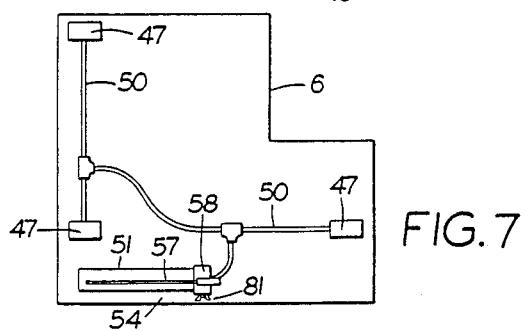
FIG. 7 is a top plan schematic view of the hydraulic jack system of the testing device.

Roller bearing testing device 1 is designed so that a single technician can conduct the testing of an axle-mounted roller bearing 2 of a stationary railcar without requiring movement of the railcar on a rail 79 (FIGS. 1 and 2). Handle 17 of testing device 1 is grasped and the device is pushed or rolled into position beneath the bearing, with outer race 72 of the bearing being located above and directly centered between idler roller 25 and drive roller 27 (FIGS. 2, 4 and 6). Motor 33 is energized and base plate 6 together with various components including rollers 25 and 27 are raised by jacks 44 upon manual manipulation of hydraulic pump handle 57 until sufficient contact force is applied to the outer race of the bearing by the drive roller to rotate the outer race at approximately 200 RPM (FIGS. 1 and 6). Idler roller 27 insures that outer race 72 is properly positioned and in engagement with drive roller 25 to rotate the bearing at the desired speed and with the correct amount of tension being applied by drive roller 25 against the outer race. Actuation of pump handle 57 forces hydraulic fluid into cylinder 45 of each jack 44 which causes pistons 46 to move downwardly and outwardly of cylinders 45 until base 49 of each piston contacts ground surface 80 or other stable support thereby causing base plate 6 to be raised. When it is desired to lower base plate 6 and rollers 25 and 27, bolt 81 is threadably rotated outwardly which removes the hydraulic pressure from pistons 46.

When testing device 1 is in contact with and rotating outer race 72 of bearing 2, an acoustic emission bearing analyzer 3 (FIG. 1) monitors acoustic emissions emanating from the bearing. One type of analyzer found suitable for use in detecting acoustic emissions is a Model 6120 Acoustic Bearing Monitor marketed by Physical Acoustics Corporation. The bearing analyzer includes a monitor 85 having a direct read meter 86 calibrated in decibels. A solid state transducer probe 87 which has a point at one end is connected to monitor 85 by a cable 88. The probe is hand-held by the technician and its point is positioned firmly against a test location, preferably at the inboard or outboard end of the bearing, particularly shown in FIG. 1 as locations 89 and 90, respectively. Acoustic emission bearing analyzer 3 of the type described above, has the capability of converting the acoustic emisssions into chart recordings or wave forms on an oscilloscope for detailed study thereof if desired.

The readings obtained from bearing analyzer 3 are then compared to those readings present in bearings containing known defects. Acoustic emission levels present which are above acceptable levels indicate serious bearing defects. Bearings exhibiting abnormal emission levels then are removed from service for repairs or replacement thereby avoiding possible failure. Acceptable levels of emissions have been determined by measuring and recording emissions from many bearings, ranging from new bearings through a wide range of defective bearings. Defective bearings also contained a wide range of types of defects, thereby making this procedure an excellent preventative maintenance policy.

The improved test device provides an extremely simple and inexpensive structure which can be operated by a single workman and moved rapidly from railcar to railcar for testing the axle bearings thereof without requiring any movement or manipulation of the railcar. Another advantage is that the drive roller is centered automatically by the associated idler driven roll as the two rollers are raised into position by the hydraulic jacks. Furthermore, the jacks automatically stabilize the base at three points thereby providing a levelling plane regardless of the particular ground slope adjacent the railcar bearing ensuring that plate 6 is horizontally level regardless of the supporting terrain. Another advantage is that the components such as the drive roller motor, gear reduction unit, drive belts, shafts, pillow blocks and the like, are readily available components which can be obtained from a variety of sources and assembled relatively easily on base plate 6 thereby eliminating complicated machining and fabrication expenses. Furthermore, the components can be easily maintained and repaired if necessary. If desired, device 1 may have a power drive motor for moving it between railcar bearings instead of requiring manual movement by handle 17 and a variety of safety guards or cages may be provided with respect to the rotating shafts and belts to increase safety for the workman should the same be desirable.

Accordingly, the improved roller bearing testing device is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness and understanding; but no unnecessary limitations are to be implied therefrom beyond the requirements of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the improved roller bearing testing device is constructed and used, the characteristics of the improved device, and the advantageous, new and useful results obtained; the new and useful structures, devices, elements, arrangements, parts, and combinations, are set forth in the appended claims.

What is claimed is:

1. A device for testing an axle-mounted roller bearing of a railcar, said device including:
   (a) first means for contacting and rotating said roller bearing;
   (b) a motor for driving the first means to rotate the roller bearing;
   (c) a base moveably supporting the first means and the motor;

(d) jack means mounted on the base for moving the first means into and out of contact with the bearing; and (e) second means for monitoring shock pulses of energy emanating from the bearing when said bearing is rotated by the motor and first means to determine possible defects in said bearing.

2. The device defined in claim 1 in which the first means comprises a drive roller and an idler roller.

3. The device defined in claim 2 in which each roller is mounted on a shaft rotatably journaled in a pair of pillow block bearings mounted on the base.

4. The device defined in claim 3 in which the motor is an electric motor having an output shaft; and in which a reduction gear operatively connects said output shaft to the drive roller for rotating said drive roller.

5. The device defined in claim 4 in which the drive roller has a first pulley operatively engaged therewith; and in which an endless drive belt drivingly connects and extends between said first pulley and a second pulley connected to the reduction gear.

6. The device defined in claim 5 in which the second pulley has a larger diameter than the first pulley.

7. The device defined in claim 2 in which the jack means comprises a plurality of hydraulically actuated jacks mounted on the base; and in which each jack has a piston which extends downwardly through an opening formed in said base.

8. The device defined in claim 7 in which three jacks are mounted on the base, with one of said jacks being positioned between the drive roller and the idler roller, and the two other of said jacks being positioned in a spaced relationship on the base.

9. The device defined in claim 8 in which the jacks are connected by hydraulic fluid lines to a manually operated hydraulic pump mounted on the base; and in which the hydraulic pump controls the movement of the jacks to move the rollers into and out of engagement with an outer race of the bearing.

10. The device defined in claim 1 in which the second means comprises a decibel measuring instrument having a solid state transducer probe; and in which the probe is adapted to contact various test points on the bearing.

11. A mobile device for rotating an axle-mounted roller bearing of a railcar for monitoring shock pulses of energy which are emitted by the rotating bearing to determine possible defects in said bearing; said device including:

(a) first means for contacting and rotating said roller bearing;

(b) a motor for driving the first means to rotate the roller bearing;

(c) a base movably supporting the first means and the motor; and (d) second means mounted on the base for moving the first means into and out of contact with the bearing.

12. The device defined in claim 11 in which the first means comprises a drive roller and an idler roller, and in which each roller is mounted on a shaft rotatably journaled in a pair of pillow block bearings mounted on the base.

13. The device defined in claim 12 in which the motor is an electric motor having an output shaft; in which a reduction gear operatively connects said output shaft to the drive roller for rotating said drive roller; in which the drive roller is operatively engaged with a first pulley which is drivingly connected to a second pulley by an endless drive belt extending therebetween; and in which the second pulley is connected to an output shaft of the reduction gear.

14. The device defined in claim 12 in which the second means comprises three hydraulically acutated jacks mounted on the base; and in which each jack has a piston which extends downwardly through an opening formed in said base, with one of said jacks being positioned between the drive roller and idler roller, and the two other of said jacks being positioned in a spaced relationship on the base.

15. The device defined in claim 14 in which the jacks are connected by hydraulic fluid lines to a hydraulic pump mounted on the base; and in which the hydraulic pump controls the movement of the jacks to move the rollers into and out of engagement with an outer race of the bearing.

16. The device defined in claim 11 in which an acoustic emission analyzer having a transducer probe is adapted to contact various test points on or adjacent the bearing as the bearing is rotated by the first means to detect shock pulses.

17. The device defined in claim 11 in which the base is mounted on a plurality of wheels and is moved by a manually operated handle pivotally mounted on said base.

18. The device defined in claim 15 in which each jack has a cylinder connected to the hydraulic fluid lines; and in which one end of said cylinder is mounted on a web-wall of an inverted generally U-shaped bracket attached to the base.

19. The device defined in claim 12 in which the rollers are mounted in a horizontal spaced relationship; and in which the rotational axis of said rollers are parallel and are located in a common horizontal plane.

20. The device defined in claim 19 in which the bearing is located intermediate of the rollers when said rollers are positioned to rotate the bearing.

* * * * *